(12) United States Patent
Oda et al.

(10) Patent No.: US 8,419,276 B2
(45) Date of Patent: *Apr. 16, 2013

(54) MOBILE X-RAY APPARATUS

(75) Inventors: Yuji Oda, Tokyo (JP); Tomokazu Takae, Tokyo (JP); Shinya Kitamura, Tokyo (JP); Tatsuo Iiyama, Kaisei-machi (JP); Kenji Takata, Kaisei-machi (JP)

(73) Assignee: Hitachi Medical Corporation, Tokyo (JP)

( * ) Notice: Subject to any disclaimer, the term of this patent is extended or adjusted under 35 U.S.C. 154(b) by 91 days.

This patent is subject to a terminal disclaimer.

(21) Appl. No.: 12/735,858

(22) PCT Filed: Nov. 20, 2008

(86) PCT No.: PCT/JP2008/071135
§ 371 (c)(1),
(2), (4) Date: Aug. 20, 2010

(87) PCT Pub. No.: WO2009/104318
PCT Pub. Date: Aug. 27, 2009

(65) Prior Publication Data
US 2010/0329426 A1    Dec. 30, 2010

(30) Foreign Application Priority Data

Feb. 22, 2008    (JP) .................................. 2008-040957

(51) Int. Cl.
*H05G 1/02*    (2006.01)
(52) U.S. Cl.
USPC ........................................................ 378/198
(58) Field of Classification Search .................. 378/167, 378/189, 197, 198, 114, 115
See application file for complete search history.

(56) References Cited

U.S. PATENT DOCUMENTS

| 4,127,775 A | * | 11/1978 | Ohlson | 378/197 |
| 2006/0120512 A1 | * | 6/2006 | Watanabe | 378/198 |
| 2006/0126795 A1 | * | 6/2006 | Lumma | 378/193 |
| 2008/0025469 A1 | | 1/2008 | Watanabe | |

FOREIGN PATENT DOCUMENTS

| JP | 04-190224 | 7/1992 |
| JP | 2004-184905 | 7/2004 |
| JP | 2006-055434 | 3/2006 |
| JP | 2007-151603 | 6/2007 |

OTHER PUBLICATIONS

Office Action in U.S. Appl. No. 12/918,627, dated Jul. 11, 2012. (7 pgs.).

* cited by examiner

*Primary Examiner* — Glen Kao
(74) *Attorney, Agent, or Firm* — Antonelli, Terry, Stout & Kraus, LLP.

(57) ABSTRACT

The present invention is directed to a mobile X-ray apparatus having a main unit, a moving carriage for installing the main unit, a column standing on the moving carriage, an X-ray generator supported by the column, and an image reader for reading X-ray image information from an imaging plate in which the X-ray image information is stored. The X-ray apparatus is provided with a brake for putting a brake on the moving carriage, a brake control means for applying the brake or releasing the brake, a read control means for prohibiting reading by the image reader, while the brake control means releases the brake, a cassette loading slot for inserting a cassette enclosing the imaging plate into the image reader, a blocking member for closing at least a part of the cassette loading slot to block the cassette to be inserted, and an open and close control means for closing the blocking member to prevent insertion of the cassette while the read control means prohibits reading.

9 Claims, 3 Drawing Sheets

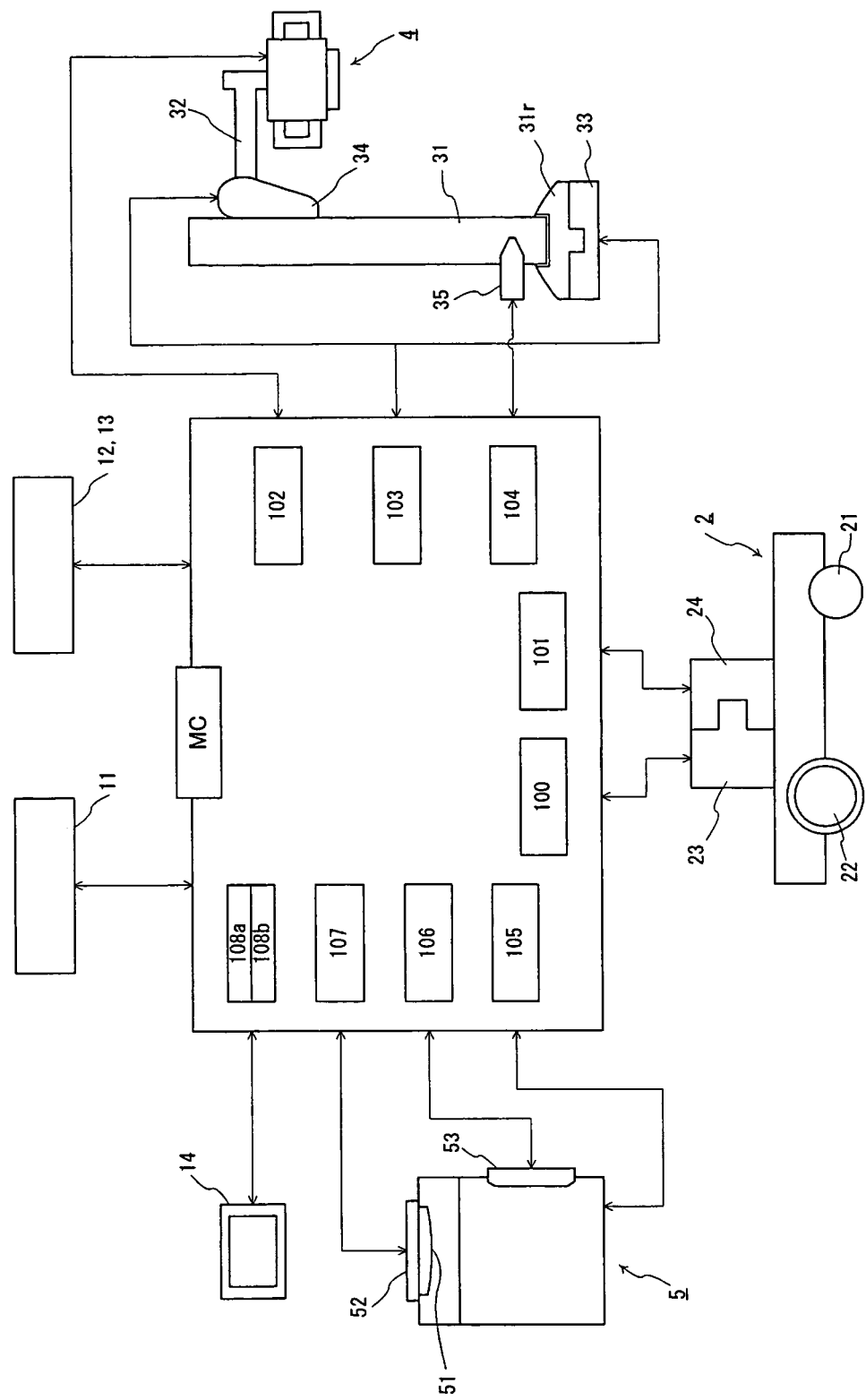
F I G. 2

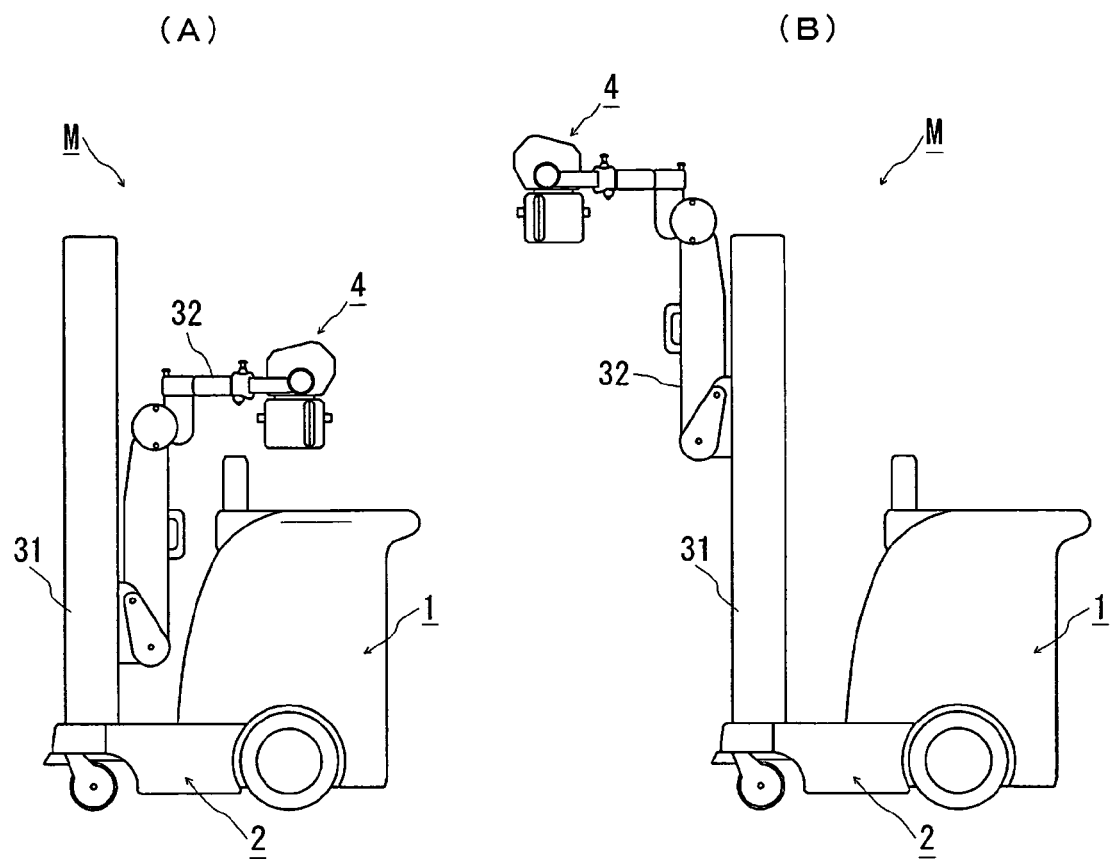
F I G. 3

MOBILE X-RAY APPARATUS

TECHNICAL FIELD

The present invention relates to a mobile X-ray apparatus which is movable in a hospital, for taking radiographs in a patient's room or the like. More particularly, it relates to the mobile X-ray apparatus which allows an X-ray image to be checked immediately at the imaging site, the X-ray image being taken by using an imaging plate (hereinafter, referred to as "IP") on which an X-ray absorption distribution of a test object is accumulated in the form of a latent image.

BACKGROUND ART

In recent years, at a medical site, there are growing needs for taking radiographs in a particular situation, such as taking radiographs of a patient in his or her room when it is difficult to move the patient out of the room, or taking radiographs urgently in an operating room. Therefore, a mobile X-ray apparatus is used widely which is movable to a patient's room or the like, for taking radiographs. Recently, another type of mobile X-ray apparatus is proceeding toward practical utilization, on which an image reader is installed for reading X-ray image information from the IP, in order that an X-ray image being taken is able to be checked immediately at the imaging site to determine on site whether or not re-radiographing is necessary.

By way of example, the patent document 1 discloses an X-ray apparatus used for round visits, which is equipped with an image information reader to read X-ray image information accumulated in the IP. This X-ray apparatus used for round visits transmits the X-ray image information read by the image information reader to a CRT display which is installed on the top of the apparatus.

In the meantime, the image reader conveys the IP in the vertical scanning direction, allowing laser light to perform scanning in the main scanning direction (being perpendicular to the vertical scanning direction), successively scans the overall IP and detects photo-stimulated luminescence at each point, thereby reading the X-ray image information. In order to obtain an accurate image, it is essential to conduct the IP conveyance and the laser scanning accurately with a high degree of precision, and the IP should not be subjected to vibration, shock, and skewing, while reading the X-ray image information.

[Patent document 1]
Japanese unexamined patent application publication No. 4-190224

DISCLOSURE OF THE INVENTION

Problem to be Solved by the Invention

In such a conventional mobile X-ray apparatus, it is possible to insert a cassette enclosing the IP and read X-ray image information from the IP after radiographing, even when the apparatus is in the state of traveling. Therefore, when an operator makes the image reader to read the X-ray image information while the mobile X-ray apparatus is traveling, there is a possibility that the X-ray image information being read is damaged due to vibration and/or shock which are caused by any traveling condition, and there is a fear that an accurate image may not be obtained.

The present invention has been made considering the situation above, and an object of the present invention is to provide a mobile X-ray apparatus which reduces a risk that the X-ray image information is damaged while being read by the image reader.

Means to Solve the Problem

The mobile X-ray apparatus according to the present invention operates the controls, establishing a link between a condition of the apparatus and a manner of operation thereof; for example, the condition of the apparatus includes a motion state or a postural state of the mobile X-ray apparatus, such as traveling state, halting state, and X-ray irradiation state, and the manner of operation includes an image reading operation and an image display operation.

More particularly, the mobile X-ray apparatus of the present invention having a main unit, a moving carriage for installing the main unit, a column standing on the moving carriage, an X-ray generator supported by the column, and an image reader for reading X-ray image information from an imaging plate in which the X-ray image information is stored, includes, a brake for putting a brake on the moving carriage, a brake control means for applying the brake or releasing the brake, a read control means for prohibiting reading by the image reader while the brake control means releases the brake, a cassette loading slot for inserting a cassette enclosing the imaging plate into the image reader, a blocking member for closing at least a part of the cassette loading slot to block the cassette to be inserted, and an open and close control means for closing the blocking member to prevent insertion of the cassette while the read control means prohibits reading.

With this configuration, in the state where the brake is released, that is, while the mobile X-ray apparatus is traveling, the image reader is not allowed to execute reading the X-ray image information. Therefore, it is possible to reduce a risk that vibration or shock may damage the X-ray image information being read. Furthermore, since the cassette is not allowed to be inserted into the image reader while the mobile X-ray apparatus is traveling, it is possible to prohibit reading by the image reader without fail.

As a brake to bring the moving carriage to a halt, there may be employed an electromagnetic brake, a disk brake, a band brake, a block brake, or a hand brake, for instance. The electromagnetic brake may be designed in such a manner that the brake is released in the state of energized, whereas it is activated in the state of non-energized, and it is highly reliable.

Generally, the mobile X-ray apparatus has a short distance between the X-ray generator and the image reader, and in some cases, X-ray irradiance is likely to be set to a high level when the radiographing is conducted in the patient's room. Therefore, if the image reader is irradiated with X-rays from the X-ray generator while reading the X-ray image information, the IP inserted in the image reader may detect leaked X-rays from the X-ray generator, and the X-ray image information stored in the IP may be damaged.

The apparatus according to the present invention is provided with a read execution decision means for making a judgment on whether or not the image reader is executing the reading, and an irradiation control means for prohibiting the irradiation of X-rays from the X-ray generator while a result of the judgment by the read execution decision means indicates that the reading is being executed.

With this configuration, there is no X-rays irradiation from the X-ray generator while the image reader performs reading of the X-ray image information, and therefore, it is possible to reduce a risk of damaging the X-ray image information stored in the IP which is currently subjected to the reading.

It is further desirable that the X-ray generator is easily manageable, since if radiographing is conducted in the patient's room or the like, there is a possibility that placement of the mobile X-ray apparatus is physically restricted due to the bed placement or an ambient environment.

Preferably, the apparatus according to the present invention is provided with an arm which is mounted on the column in such a manner as movable up and down, the tip of the arm being equipped with the X-ray generator, and a rotating mechanism which allows the column to be rotatable about the axis thereof.

However, if the column rotates or the arm move up and down while the image reader performs reading of X-ray image information, there is a possibility that vibration and/or shock generated by such motions may damage the X-ray image information being read.

The apparatus according to the present invention which facilitates manageability of the X-ray generator may be provided with an electromagnetic brake for bringing the up-and-down movement of the arm to a halt and an electromagnetic brake for bringing the rotation of the column to a halt, and further a support mechanism control means for activating or releasing these electromagnetic brakes. It is further possible to configure such that the read control means prohibits reading while the support mechanism control means releases either the electromagnetic brakes.

With this configuration, the image reader is not allowed to read the X-ray image information while performing the up-and-down operation of the arm and the rotating operation of the column. Therefore, it is possible to reduce the risk that the X-ray image information being read is damaged due to any vibration and shock.

Preferably, the apparatus has a configuration including the read execution decision means for making a judgment on whether or not the image reader is executing the reading, and while a result of the judgment by the read execution decision means indicates that the reading is being executed, the support mechanism control means activates both of the electromagnetic brakes to block the up-and-down movement of the arm and the rotation of the column.

With this configuration, the up-and-down operation of the arm and the rotating operation of the column are not allowed while the image reader performs reading of the X-ray image information. Therefore, it is possible to further reduce the risk that vibration and/or shock may damage the X-ray image information being read.

In recent years, an issue of personal information protection draws increasing attention. For example, it is not preferable to keep the X-ray image of a patient to be displayed on a display (monitor) when the mobile X-ray apparatus moves from room to room, because there is a high risk of disclosing the personal information of the patient to others.

The apparatus according to the present invention may be provided with a monitor for displaying an X-ray image generated from the X-ray image information read by the image reader, and a first display control means which hides the X-ray image while the brake control means releases the brake.

With this configuration, since the X-ray image is not displayed while the mobile X-ray apparatus is traveling, it is possible to reduce the risk that the personal information leaks.

The apparatus according to the present invention in which the X-ray generator is easily manageable, includes, a posture decision means for making a judgment on whether a traveling posture is taken in which the X-ray generator is located above the moving carriage, or an imaging posture is taken in which the X-ray generator projects from the moving carriage, a monitor for displaying an X-ray image generated from the X-ray image information which is read by the image reader, and a second display control means for hiding the X-ray image while a result of the judgment by the posture decision means indicates the traveling posture.

With this configuration, while the mobile X-ray apparatus maintains the traveling posture, the X-ray image is not displayed on the monitor irrespective of whether the mobile X-ray apparatus is traveling or not. Therefore, it is possible to reduce the risk that the personal information may leak. By way of example, even though there happens to be a situation where an operator leaves the mobile X-ray apparatus on the way, there is no worry that others may steal a glance at the X-ray image.

The mobile X-ray apparatus according to the present invention may include, an arm mounted on the column in such a manner as movable up and down, and equipped with the X-ray generator on the tip of the arm, a rotating mechanism which allows the column to be rotatable about the axis thereof, a posture decision means for making a judgment on whether a traveling posture is taken in which the X-ray generator is located above the moving carriage, or an imaging posture is taken in which the X-ray generator projects from the moving carriage, a monitor for displaying an X-ray image generated from the X-ray image information which is read by the image reader, and a second display control means for hiding the X-ray image while a result of the judgment by the posture decision means indicates the traveling posture.

With the configuration above, the X-ray generator is easily manageable, and further, the X-ray image is not displayed on the monitor while the mobile X-ray apparatus is traveling. Therefore, it is possible to reduce the risk that the personal information may leak.

Effect of the Invention

Since the mobile X-ray apparatus of the present invention does not allow the image reader to execute reading of the X-ray image information during the traveling motion, it is possible to reduce the risk that vibration and/or shock damages the X-ray image information which is read from the IP. Furthermore, the mobile X-ray apparatus according to the present invention is able to reduce the risk that the IP being subjected to reading of the X-ray image information is damaged by coming into contact with various components within the image reader due to vibration and/or shock.

BEST MODE FOR CARRYING OUT THE INVENTION

With reference to the accompanying drawings, embodiments of the present invention will be explained. FIG. 1 is a rear perspective view of the mobile X-ray apparatus relating to the present embodiment, and FIG. 2 is a functional block diagram of the mobile X-ray apparatus. FIG. 3(A) is a schematic view for explaining the traveling posture of the mobile X-ray apparatus relating to the present embodiment, and FIG. 3(B) is a schematic view for explaining the imaging posture of the mobile X-ray apparatus relating to the present embodiment.

[Configuration of the Mobile X-Ray Apparatus]

The mobile X-ray apparatus M according to the present invention includes a main unit 1, a moving carriage 2, a support mechanism 3, an X-ray generator 4, and an image reader 5 (FIG. 1). A cassette which stores an IP is used during the time the radiographing is conducted. Specifically, an imaging object is placed between the X-ray generator and the cassette (IP), and the radiographing is conducted by irradiating X-rays from the X-ray generator and storing in the IP the X-rays which have transmitted the imaging object.

An operation panel 11, a handle 12, and a monitor 14 are installed on the main unit 1, for manipulating various equipment and devices mounted on the mobile X-ray apparatus M. The main unit 1 further accommodates a power source. In addition, the main unit 1 incorporates a main controller MC. The main controller MC is connected to various equipment and devices (FIG. 2). Arrows in FIG. 2 indicate inputting and outputting of signals (data), and various equipment and devices operate in response to the signals from the main controller MC.

The moving carriage 2 is equipped with a pair of front wheels 21 and a pair of rear wheels 22. The front wheels 21 are casters being swingable, and the rear wheels 22 are drive wheels which are driven by a motor 23 being mounted on the moving carriage 2. The motor 23 is rotatable both normally and reversely, and the rotation of an output shaft is transferred to the rear wheels 22, thereby driving (rotating) the rear wheels 22.

An electromagnetic brake 24 is installed on the output shaft of the motor 23. The electromagnetic brake 24 is a power-off activated electromagnetic brake. While not energized, the electromagnetic brake 24 allows the output shaft to generate braking force and puts a brake on (stops) the rear wheels 22. Accordingly, the brake is activated.

During the time the moving carriage 2 (the mobile X-ray apparatus M) is made to travel, an operator holds the handle 12 for operation. The handle 12 is provided with a brake release switch 13. While the switch 13 is depressed, the electromagnetic brake 24 is energized and the brake is released. When the switch 13 is released, the energization to the electromagnetic brake 24 is interrupted, and the brake is activated. Therefore, during the time the moving carriage 2 is made to move, the operator performs the operation to hold the handle 12 in such a manner that the brake release switch 13 is kept depressed.

In addition, a pressure sensor is incorporated in each of both ends of the handle 12. When the handle 12 is pushed forward, the motor 23 is rotated normally and allows the moving carriage 2 to move forward. When the handle 12 is pulled backward, the motor 23 is rotated reversely, and allows the moving carriage to move backward.

In order to put a brake on (stop) the moving carriage 2, the operator returns the handle 12 to the middle position, and takes off the brake release switch 13. Then, power distribution from the motor 23 to the electromagnetic brake 24 is interrupted, and then, rotation of the motor 23 is stopped, and the brake is activated. The motor control means 100 incorporated in the main controller MC allows the motor 22 to be driven or stopped, and the brake control means 101 incorporated in the main controller MC allows the electromagnetic brake 23 to be activated or released.

The support mechanism 3 is a mechanism to support the X-ray generator 4, and it is provided with a column 31 and an arm 32. The column 31 is made to stand on the moving carriage 2, and a rotating mechanism 31*r* which allows the column 31 to be rotatable about the axis thereof, and an electromagnetic brake 33 for putting a brake on the rotation of the column are installed on the place where the column 31 is mounted on the moving carriage 2. The arm 32 is mounted on the column 31 in such a manner as movable up and down. An electromagnetic brake 34 for putting a brake on the up and down movement of the arm is mounted on the place where the arm 32 is installed on the column 31. These electromagnetic brakes 33 and 34 are power-off activated electromagnetic brakes, and the brake is activated during de-energization, thereby fixing a rotation angle of the column 31 and a position of the up-and-down movement of the arm 32. Furthermore, the X-ray generator 4 is mounted on the tip of the arm 31.

The column 31 supports the X-ray generator 4 via the arm 32. The X-ray generator 4 has an X-ray tube 41 for generating X-rays, and a movable X-ray diaphragm device 42 is mounted on the opening for X-ray irradiation. The main controller MC stores an irradiation control means 102 for permitting or prohibiting the irradiation of X-rays from the X-ray generator 4. While the irradiation control means 102 prohibits the irradiation of X-rays, the X-ray generator 4 is not allowed to irradiate X-rays.

In order to adjust the rotation angle of the column 31 or the up-and-down position of the arm 32, so as to control the position of the X-ray generator 4, an operator grasps and manipulates the handle 43 which is provided on the X-ray generator 4. An arm fixation release switch 44 is provided on the handle 43. While the arm fixation release switch 44 is depressed, each of the electromagnetic brakes 33 and 34 is energized to release the brake, whereas the arm fixation release switch 44 is released, the energization to each of the electromagnetic brakes 33 and 34 is interrupted and the brake is activated. Accordingly, when the position of the X-ray generator 4 is adjusted, the operator grasps and manipulates the handle 43 in such a manner that the arm fixation release switch 44 is kept depressed. Then, the operator adjusts the rotation angle of the column 31 and the up-and-down position of the arm 32 to locate the X-ray generator 4, and thereafter the arm fixation release switch 44 is released. Accordingly, each of the electromagnetic brakes 33 and 34 is activated, thereby fixing the rotation angle of the column 31 and the up-and-down position of the arm 32. The support mechanism control means 103 stored in the main controller MC performs activation or release of each of the electromagnetic brakes 33 and 34.

The mobile X-ray apparatus M rotates the column 31 about the axis, thereby turning the arm 32 about the axis of the column 31. Accordingly, it is possible to do switching between the traveling posture (FIG. 3(A)) and the imaging posture (FIG. 3(B)). The traveling posture (FIG. 3(A)) is a posture in which the X-ray generator 4 is positioned above the main unit 1 (moving carriage 2). The imaging posture (FIG. 3(B)) is a posture in which the X-ray generator 4 projects from the moving carriage 2. On the bottom of the column 31, there is installed a posture sensor 35 for detecting a rotating angle of the column. A posture decision means 104 stored in the main controller MC makes a judgment on whether the traveling posture is taken or the imaging posture is taken.

The image reader 5 reads X-ray image information from the IP on which the X-ray image information is stored. The image reader 5 is incorporated in the main unit 1, and the main unit 1 is provided with a cassette loading slot 51 for inserting a cassette into the image reader 5. When the cassette is inserted, the image reader 5 starts reading the X-ray image information. The image reader 5 takes out the IP from the cassette being inserted, and reads X-ray image information from the IP. Subsequently, the image reader 5 erases the X-ray image information which remains in the IP as to which reading has been completed. The main controller MC incorporates a read control means 105 which permits or prohibits reading by the image reader 5. While the read control means 105 prohibits reading, the image reader 5 is not allowed to read the X-ray image information. In addition, the image reader 5 is provided with a cassette detection sensor 53 which detects that the cassette is inserted in the image reader. A read execution decision means 106 incorporated in the main controller MC makes judgment on whether or not the image reader 5 executes the reading.

An openable and closable cover (blocking member) 52 is mounted on the cassette loading slot 51. The state where the cover is open enables the cassette to be inserted, and the state where the cover is closed disables the insertion of the cassette. An open and close control means 107 incorporated in the main control unit MC performs the opening and closing of the cover 52. The present embodiment employs the cover for blocking the insertion of the cassette, but it is not limited to this example. A movable protrusion may be applicable. By way of example, if such movable protrusion is employed, it is provided in such a manner that the state where the protrusion moves forward to the cassette loading slot closes a part of the loading slot and disables the cassette to be inserted, whereas the state where the protrusion moves backward from the cassette loading slot enables the insertion of the cassette.

The X-ray image information read by the image reader 5 is stored in a storage unit, not illustrated, via the main controller MC. The main controller MC generates an X-ray image from the X-ray image information that the image reader 5 has read, and displays the X-ray image on the monitor 14. Besides the X-ray image, the monitor 14 displays setting screens of the X-ray generator 4 and the image reader 5, patient information and inspection information which are acquired from the RIS (Radiology Information System). In addition, the monitor 14 is equipped with a touch panel. The operator uses the touch panel to configure settings of the X-ray generator 4 and the image reader 5, and input the patient information and the like.

The main controller MC incorporates a first display control means 108*a* and a second display control means 108*b* for displaying or hiding the X-ray image. While the first display control means 108*a* or the second display control means 108*b* hides the X-ray image, there is no X-ray image displayed on the monitor 14.

Embodiments employing the aforementioned mobile X-ray apparatus M will be explained. In the mobile X-ray apparatus M, while the brake control means 101 releases the electromagnetic brake 24, the read control means 105 prohibits reading by the image reader 5, according to the main controller MC.

Embodiment 1-1

In the present embodiment, there will be explained a case as an example that an operator tries to make the image reader 5 to perform reading operation, while the operator is manipulating the handle 12 to keep the mobile X-ray apparatus M in travel motion.

While the mobile X-ray apparatus M is traveling, the brake control means 101 releases the electromagnetic brake 24. Therefore, even though a cassette is inserted in the image reader 5 during the time the mobile X-ray apparatus M is traveling, the read control means 105 prohibits the image reader 5 from conducting the reading, and therefore, the image reader 5 is not allowed to read the X-ray image information. While the brake control means 101 activates the electromagnetic brake 24 (the mobile X-ray apparatus M is static), the read control means 105 allows reading by the image reader 5. Accordingly, the image reader 5 reads the X-ray image information while the mobile X-ray apparatus M in the halting state.

As thus described, the mobile X-ray apparatus M does not allow reading of the X-ray image information during the traveling motion. In other words, reading of the X-ray image information is allowed while the apparatus is in the state of halt; thereby reducing a risk that the X-ray image information in the course of being read from the IP is damaged due to vibration and/or shock. In addition, since the reading of the X-ray image information is not allowed during the traveling motion, it is further possible to reduce a risk that the IP being subjected to reading is damaged by coming into contact with various components within the image reader due to vibration and/or shock.

The image reader 5 employed in the present embodiment has a configuration that insertion of the cassette triggers reading of the X-ray image information. In addition, the effect of the present invention may be achieved by using another image reader having a configuration, for example, reading is initiated according to an operation to start the reading, after the cassette has been inserted.

Furthermore, the image reader 5 erases the X-ray image information which remains in the IP after reading of the image is completed. Then, the read control means 105 prohibits reading of the X-ray image information, and simultaneously prohibits erasing of the X-ray image information, thereby suppressing the occurrence of failure in erasing due to vibration and/or shock. The same can be applied to the embodiment 3-1 which will be described below.

Embodiment 1-2

In the present embodiment, similar to the embodiment 1-1, there will be explained a case as an example that an operator tries to make the image reader 5 to perform reading operation, while the operator keeps the mobile X-ray apparatus M in traveling motion. Furthermore, in the present embodiment, according to the main controller MC, while the read control means 105 prohibits reading by the image reader 5, the open and close control means 107 closes the cover 52 and blocks the insertion of the cassette.

As explained in the embodiment 1-1, while the mobile X-ray apparatus M takes the traveling motion, the read control means 105 prohibits reading by the image reader 5. Even though the operator tries to insert a cassette in the image reader 5 while the reading is prohibited, the open and close control means 107 closes the cover 52 on the cassette loading slot 51 to block the insertion of the cassette. Therefore, the image reader 5 is not allowed to execute reading of the X-ray image information.

On the other hand, while the brake control means 101 activates the electromagnetic brake 24, the read control means 105 allows the image reader 5 to perform reading, and the open and close means 107 sets the cover 52 to be open. Therefore, insertion of the cassette from the cassette loading slot 51 is enabled. Therefore, during the halts of the mobile X-ray apparatus M, the image reader 5 is allowed to execute reading the X-ray image information.

In particular, according to the embodiment 1-2, even though the operator tries to insert the cassette in the image reader 5, insertion of the cassette is not allowed during the traveling motion. Therefore, it is possible to prevent with reliability that the image reader 5 performs reading operation during the traveling motion. Furthermore, since the insertion of the cassette into the image reader 5 is disabled during the traveling motion, it is possible to prevent that the IP comes into contact with various components within the reader and gets damaged due to vibration and/or shock.

Embodiment 2

In the present embodiment, there will be explained a case as an example that an operator tries to perform an operation for allowing the X-ray generator 4 to irradiate X-rays, while the image reader 5 executes reading of the X-ray image information. In the embodiment 2, according to the main controller MC, the irradiation control means 102 prohibits irradiation of X-rays while a result of the judgment by the read execution decision means 106 indicates that the reading is being executed.

While a cassette is inserted into the image reader 5 and reading of the X-ray image information is started and executed, the read execution decision means 106 determines that the reading is being executed. During this time, even though it is tried to make the X-ray generator 4 to irradiate X-rays, the irradiation control means 102 prohibits the X-ray irradiation, and therefore no X-rays are irradiated from the X-ray generator 4.

According to the embodiment 2, while the image reader 5 performs reading of the X-ray image information, the X-ray generator 4 is not allowed to irradiate X-rays. Therefore, it is possible to prevent a damage of the X-ray image information, which is stored in the IP being subjected to the reading, due to an influence of leaked X-rays.

Embodiment 3-1

In the present embodiment, there will be explained a case as an example that an operator tries to perform the reading operation by the image reader 5 while performing an operation for rotating the column 31 or performs up-and-down moving operation of the arm 32, in order to adjust the position of the X-ray generator 4.

In the embodiment 3-1, according to the main controller MC, while the support mechanism control means 103 releases both the electromagnetic brakes 33 and 34, the read control means 105 prohibits reading by the image reader 5.

While the operator performs the operation for rotating the column 31 or the operation for moving the arm 32 up and down, the support mechanism control means 103 releases the electromagnetic brakes 33 and 34. During this time, even though a cassette is inserted in the image reader 5, the read control means 105 prohibits reading by the image reader 5. Therefore, the image reader 5 is not allowed to execute reading of the X-ray image information.

According to the embodiment 3-1, while the column 31 is rotating or the arm is moving up and down, reading of the X-ray image information is not performed. Therefore, it is possible to reduce a risk that the X-ray image information being subjected to the reading from the IP is damaged by vibration and/or shock.

Embodiment 3-2

In the embodiment 3-2, in addition to the configuration as explained in the embodiment 3-1, an explanation will be made as to the configuration that according to the main controller MC, the support mechanism control means 103 activates both the electromagnetic brakes 33 and 34 and blocks the up-and-down movement of the arm and the rotation of the column, while the result of the judgment by the read execution decision means 106 indicates that the reading is being executed.

While the cassette is inserted in the image reader 5 and reading of the X-ray image information is started and executed, the read execution decision means 106 determines that the reading is being executed. At this time, even though the operation for rotating the column or the operation for moving the arm up and down are tried to be performed, the support mechanism control means 103 activates the electromagnetic brakes 33 and 34, and therefore, the rotation angle of the column 31 and the up-and-down position of the arm 32 are fixed.

According to the embodiment 3-2, while the image reader 5 performs reading of the X-ray image information, the column 31 does not rotate or the arm 32 does not move up and down. Therefore, it is possible to prevent that the X-ray image information being subjected to reading from the IP is damaged due to vibration and/or shock.

When the electromagnetic brake is released, a large amount of incoming current flows and static electricity may be generated. In particular, if the image reader 5 is incorporated in the forward part of the main unit 1 (on the side of the column 31), it is conceivable that the X-ray image information stored in the IP which is inserted in the image reader 5 is damaged by the influence of the static electricity. However, according to the embodiment 3-2, while the cassette is inserted in the image reader 5 and reading of the X-ray image information is started and executed, neither of the electromagnetic brakes 33 and 34 is released. Therefore, it is possible to reduce the risk that the static electricity may damage the X-ray image information which is stored in the IP being subjected to reading.

Furthermore, in order to prevent the damage on the IP as much as possible, it is preferable that while the read control means 105 prohibits reading, the open and close control means 107 closes the cover 52 of the cassette loading slot 51, thereby blocking the insertion of the cassette.

Embodiment 4-1

In the present embodiment, there will be explained a case as an example that the operator tries to allow the mobile X-ray apparatus M to move (travel) in the state that the X-ray image is kept displayed in the monitor 14. In the embodiment 4-1, according to the main controller MC, the first display control means 108a hides the X-ray image, while the brake control means 101 releases the electromagnetic brake 24.

When the mobile X-ray apparatus M is made to travel, the brake control means 101 releases the electromagnetic brake 24. On this occasion, the first display control means 108a switches the mode for displaying the X-ray image to non-display state, and the X-ray image having been displayed in the monitor 14 becomes hidden.

According to the embodiment 4-1, while the mobile X-ray apparatus is traveling, the X-ray image is not displayed on the monitor 14. Therefore, it is possible to reduce a risk that personal information may leak out while the apparatus is moving.

Embodiment 4-2

In the present embodiment, there will be explained a case as an example that the operator allows the mobile X-ray apparatus M to move in the state that the mobile X-ray apparatus M is switched to the traveling posture. In the embodiment 4-2, according to the main controller MC, while the result of the judgment by the posture decision means 104 indicates the traveling posture, the second display control means 108b hides the X-ray image.

After imaging is completed, the mobile X-ray apparatus M is switched from the imaging posture to the traveling posture, whereby the X-ray generator 4 becomes stored in the upper side of the moving carriage 2, facilitating the move of the mobile X-ray apparatus M (see FIG. 3). While the posture decision means 104 determines that the posture is the traveling posture, the second display control means 108b switches the mode for displaying the X-ray image to non-display mode, thereby making the X-ray image having been displayed in the monitor 14 becomes hidden.

According to the embodiment 4-2, while the mobile X-ray apparatus M maintains the traveling posture, the X-ray image is not displayed in the monitor 14, regardless of whether the mobile X-ray apparatus M is traveling or not. By way of example, even in the case where the operator leaves the mobile X-ray apparatus M in the course of moving, there is no worry that others may steal a glance at the X-ray image, and it is possible to prevent with reliability that personal information may leak out while moving.

While the X-ray image is set to be non-display state, only the X-ray image may be hidden. Alternatively, other information such as patient information, which is displayed simultaneously with the X-ray image, may be hidden as well. In addition, it is preferable that the setting screen of the X-ray generator 4 and the like is allowed to be displayed, so as to make preparations for the next imaging in the course of moving.

As explained in the embodiments 4-1 and 4-2, a technical idea that when the mobile X-ray apparatus is moved, the X-ray image is not displayed by using the first display control means or the second display control means, may be applicable to all kinds of mobile X-ray apparatus provided with an X-ray output part for outputting X-ray image information, which is obtained by irradiating X-rays from the X-ray generator, transmitting through an imaging object. By way of example, in addition to the mobile X-ray apparatus which is able to display the X-ray image, taken by using the IP and the image reader according to the present invention, the technique may also be applied to another mobile X-ray apparatus which is able to display the X-ray image taken by using an FPD (Flat Panel Detector).

Those embodiments of the present invention described above are just examples, and the present invention is not limited to those embodiments. It is intended that the invention embrace various modifications that fall within the spirit and scope of the present invention. By way of example, a mobile X-ray apparatus operated by hand is also applicable, in which the moving carriage is not provided with drive wheels. A brake used in the hand-operated mobile X-ray apparatus may be a band brake or a block brake, which may deliver performance in putting a brake. A publicly known hand brake may be used as the brake for the hand-operated mobile X-ray apparatus, which is provided for ensuring the safety when the mobile X-ray apparatus moves.

INDUSTRIAL APPLICABILITY

The mobile X-ray apparatus of the present invention is preferably applicable for a mobile X-ray apparatus which is used for round visits.

BRIEF DESCRIPTION OF DRAWINGS

FIG. 2 is a functional block diagram of the mobile X-ray apparatus relating to the present embodiment; and FIG. 3(A) is a schematic view for illustrating the traveling posture of the mobile X-ray apparatus relating to the present embodiment, and FIG. 3(B) is a schematic view for illustrating the imaging posture of the mobile X-ray apparatus relating to the present embodiment.

DENOTATION OF REFERENCE NUMERALS

Figure 1:
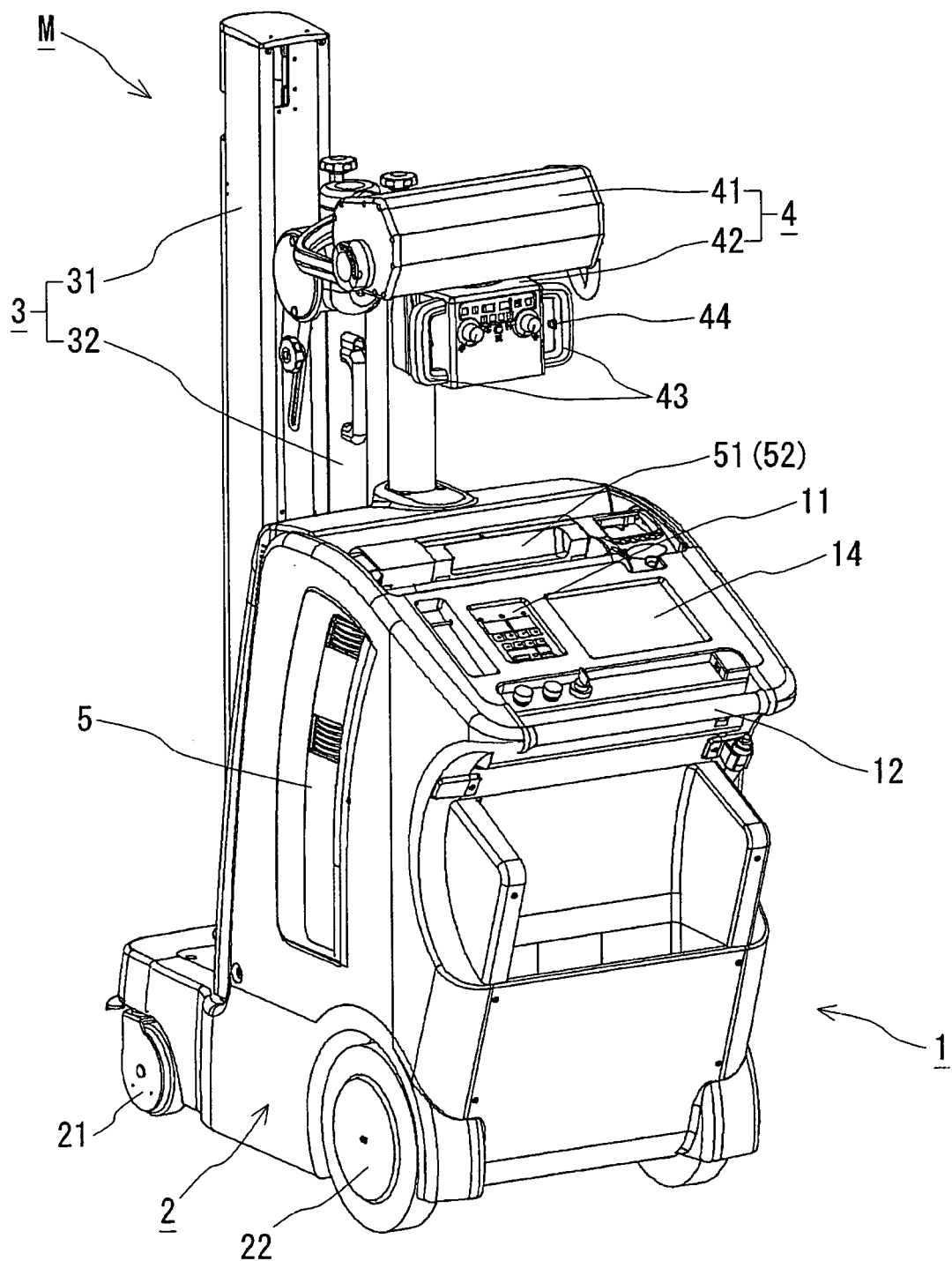
FIG. 1 is a rear perspective view of the mobile X-ray apparatus relating to the present embodiment.

M: MOBILE X-RAY APPARATUS, 1: MAIN UNIT, 11: OPERATION PANEL, 12: HANDLE, 13: BRAKE RELEASE SWITCH, 14: MONITOR, 2: MOVING CARRIAGE, 21: FRONT WHEEL, 22: REAR WHEEL, 23: MOTOR, 24: ELECTROMAGNETIC BRAKE, 3: SUPPORT MECHANISM, 31: COLUMN, 32: ARM, 31r: ROTATING MECHANISM, 33, 34: ELECTROMAGNETIC BRAKE, 35: POSTURE SENSOR, 4: X-RAY GENERATOR, 41: X-RAY TUBE, 42: MOVABLE X-RAY DIAPHRAGM DEVICE, 43: HANDLE, 44: ARM FIXATION RELEASE SWITCH, 5: IMAGE READER, 51: CASSETTE LOADING SLOT, 52: COVER, 53: CASSETTE DETECTION SENSOR, MC: MAIN CONTROLLER, 100: MOTOR CONTROL MEANS, 101: BRAKE CONTROL MEANS, 102: IRRADIATION CONTROL MEANS, 103: SUPPORT MECHANISM CONTROL MEANS, 104: POSTURE DECISION MEANS, 105: READ CONTROL MEANS, 106: READ EXECUTION DECISION MEANS, 107: OPEN AND CLOSE CONTROL MEANS, 108a: FIRST DISPLAY CONTROL MEANS, 108b: SECOND DISPLAY CONTROL MEANS

What is claimed is:

1. A mobile X-ray apparatus having a main unit, a moving carriage for installing the main unit, a column standing on the moving carriage, an X-ray generator supported by the column, and an image reader for reading X-ray image information from an imaging plate in which the X-ray image information is stored, comprising,
   a brake for putting a brake on the moving carriage,
   a brake control means for applying the brake or releasing the brake,
   a read control means for prohibiting reading by the image reader while the brake control means releases the brake,
   a cassette loading slot for inserting a cassette enclosing the imaging plate into the image reader,
   a blocking member for closing at least a part of the cassette loading slot to block the cassette to be inserted, and
   an open and close control means for closing the blocking member to prevent insertion of the cassette while the read control means prohibits reading.

2. The mobile X-ray apparatus according to claim 1, wherein, the brake is any one of the followings, an electromagnetic brake, a disk brake, a band brake, a block brake, and a hand brake.

3. The mobile X-ray apparatus according to claim 1, further comprising,
   a read execution decision means for making a judgment on whether or not the image reader is executing the reading, and
   an irradiation control means for prohibiting the irradiation of X-rays from the X-ray generator while a result of the judgment by the read execution decision means indicates that the reading is being executed.

4. The mobile X-ray apparatus according to claim 1, further comprising,
   an arm which is mounted on the column in such a manner as movable up and down, the tip of the arm being equipped with the X-ray generator, and
   a rotating mechanism which allows the column to be rotatable about the axis an axis thereof.

5. The mobile X-ray apparatus according to claim 4, further comprising an electromagnetic brake for bringing the up-and-down movement of the arm to a halt and an electromagnetic brake for bringing the rotation of the column to a halt, and a support mechanism control means for activating or releasing these electromagnetic brakes, wherein, the read control means prohibits reading by the image reader, while the support mechanism control means releases the electromagnetic brake for bringing the up-and-down movement of the arm to a halt and the electromagnetic brake for bringing the rotation of the column to a halt.

6. The mobile X-ray apparatus according to claim 5, further comprising a read execution decision means for making a judgment on whether or not the image reader is executing the reading, wherein, while a result of the judgment by the read execution decision means indicates that the reading is being executed, the support mechanism control means activates the electromagnetic brake for bringing the up-and-down movement of the arm to a halt and the electromagnetic brake for bringing the rotation of the column to a halt, so as to block the up-and-down movement of the arm and the rotation of the column.

7. The mobile X-ray apparatus according to claim 1, further comprising, a monitor for displaying an X-ray image generated from the X-ray image information read by the image reader, and a display control means for hiding the X-ray image while the brake control means releases the brake.

8. The mobile X-ray apparatus according to claim 1, further comprising, a posture decision means for making a judgment on whether a traveling posture is taken in which the X-ray generator is located above the moving carriage, or an imaging posture is taken in which the X-ray generator projects from the moving carriage, a monitor for displaying an X-ray image generated from the X-ray image information which is read by the image reader, and a display control means for hiding the X-ray image while a result of the judgment by the posture decision means indicates the traveling posture.

9. The mobile X-ray apparatus according to claim 1, further comprising, an arm mounted on the column in such a manner as movable up and down, and equipped with the X-ray generator on the tip of the arm, a rotating mechanism which allows the column to be rotatable about an axis thereof, a posture decision means for making a judgment on whether a traveling posture is taken in which the X-ray generator is located above the moving carriage, or an imaging posture is taken in which the X-ray generator projects from the moving carriage, a monitor for displaying an X-ray image generated from the X-ray image information which is read by the image reader, and a display control means for hiding the X-ray image while a result of the judgment by the posture decision means indicates the traveling posture.

* * * * *